(12) United States Patent
Reis et al.

(10) Patent No.: US 9,909,975 B1
(45) Date of Patent: Mar. 6, 2018

(54) DEVICE FOR ROTATION ABOUT AN AXIS OF ROTATION TO DRIVE LIQUID FLOW WITHIN THE DEVICE COMPRISING A FIRST ELEMENT, A SECOND ELEMENT AND THE RADIALLY OUTER WALL OF A CAVITY DEFINE A DETECTION CHAMBER

(71) Applicant: Biosurfit, SA, Lisbon (PT)

(72) Inventors: Nuno Alexandre Esteves Reis, Lisbon (PT); Tania Moura Pires De Andrade Tenreiro, Lisbon (PT); Miguel Joao Marques Barreiros, Lisbon (PT)

(73) Assignee: Biosurfit, S.A., Lisbon (PT)

( * ) Notice: Subject to any disclaimer, the term of this patent is extended or adjusted under 35 U.S.C. 154(b) by 0 days.

(21) Appl. No.: 15/626,592

(22) Filed: Jun. 19, 2017

(30) Foreign Application Priority Data

Oct. 7, 2016 (GB) .................................... 1617081.3
Oct. 7, 2016 (PT) ......................................... 109663

(51) Int. Cl.
*G01N 21/07* (2006.01)
*G01N 21/05* (2006.01)
(Continued)

(52) U.S. Cl.
CPC .......... *G01N 21/05* (2013.01); *B01L 3/50273* (2013.01); *B01L 3/502715* (2013.01);
(Continued)

(58) Field of Classification Search
CPC .... G01N 21/85; G01N 21/07; G01N 21/0303; G01N 35/025; G01N 2015/045; G01N 2201/0415; B01L 3/5207; B04B 5/02
(Continued)

(56) References Cited

U.S. PATENT DOCUMENTS 4,330,206 A       5/1982   Gausmann et al.
5,173,262 A *  12/1992   Burtis ............... B01L 3/502753
                                                                    422/50
(Continued)

FOREIGN PATENT DOCUMENTS

EP        1 752 758 A1    2/2007
EP          1752759 B1    5/2012
(Continued)

OTHER PUBLICATIONS

M. Grumann et al., "Direct Hemoglobin Measurement by Monolithically Integrated Optical Beam Guidance", Jun. 5, 2005, 4 pages.

(Continued)

*Primary Examiner* — Que T Le
(74) *Attorney, Agent, or Firm* — Patterson Thuente Pedersen, P.A.

(57) ABSTRACT

A device configured for rotation about an axis of rotation to drive liquid flow within the device. The device includes a detection chamber having opposed first second ends and two optical features defining an optical path through the detection chamber, between the first and second ends. The detection chamber includes a first liquid inlet disposed at the first end on a first side of the optical path, a first liquid outlet disposed at the second end of the detection chamber on the first side of the optical path and a second liquid outlet disposed at the second end of the detection chamber on a second side of the optical path. The first side of the optical path is radially outwards of the second side of the optical path.

4 Claims, 5 Drawing Sheets

(51) Int. Cl.
   *G01N 21/552*   (2014.01)
   *G01N 33/49*    (2006.01)
   *B01L 3/00*     (2006.01)

(52) U.S. Cl.
   CPC ........... *G01N 21/552* (2013.01); *G01N 33/49* (2013.01); *B01L 2300/0654* (2013.01); *B01L 2300/0848* (2013.01); *B01L 2300/168* (2013.01); *B01L 2400/0409* (2013.01); *G01N 2201/068* (2013.01)

(58) Field of Classification Search
   USPC ................................................ 250/239, 573
   See application file for complete search history.

(56) References Cited

U.S. PATENT DOCUMENTS

| 5,186,896 A | 2/1993 | Bouchée et al. |
| 2013/0023060 A1 | 1/2013 | Klaunik et al. |
| 2016/0214104 A1 | 7/2016 | Schwemmer et al. |

FOREIGN PATENT DOCUMENTS

| EP | 2817519 B1 | 12/2014 |
| WO | WO 2010/077159 A1 | 7/2010 |
| WO | WO 2012/133750 A1 | 10/2012 |

OTHER PUBLICATIONS

M. Grumann et al., "Optical Beam Guidance in Monolithic Polymer Chips for Miniaturized Colorimetric Assays", Jan. 30, 2005, 4 pages.
Search Report dated Oct. 7, 2016 for Portuguese Application No. 109663, 3 pages.
Robert Gorkin III et al., "Pneumatic pumping in centrifugal microfluidic platforms", Feb. 17, 2010, 10 pages.
Jens Ducrée et al., "The centrifugal microfluid Bio-Disk platform", Jun. 28, 2007, 13 pages.
Maximilian Focke et al., "Centrifugal microfluidic system for primary amplification and secondary real-time PCR", Sep. 14, 2010, 3 pages.
Search Report and Written Opinion dated Nov. 23, 2017 for PCT Application No. PCT/EP2017/037649, 26 pages.

* cited by examiner

DEVICE FOR ROTATION ABOUT AN AXIS OF ROTATION TO DRIVE LIQUID FLOW WITHIN THE DEVICE COMPRISING A FIRST ELEMENT, A SECOND ELEMENT AND THE RADIALLY OUTER WALL OF A CAVITY DEFINE A DETECTION CHAMBER

RELATED APPLICATIONS

The present application claims priority to Great Britain Application No. 1617081.3 filed Oct. 7, 2016 and Portuguese Application No. 109663 filed Oct. 7, 2016, each of which is hereby incorporated herein in its entirety by reference.

FIELD OF THE DISCLOSURE

The present invention relates to the handling of liquids and, in particular, to a detection chamber for use in obtaining an optical measurement of liquid in the detection chamber.

BACKGROUND OF THE DISCLOSURE

Obtaining optical measurements (for example a light absorption, reflection or scattering measurement) of a liquid is a useful tool in many applications. In particular, optical measurements may be used to determine characteristics (absorbance, turbidity) of a sample or a component of a sample; or to monitor the kinetics of a reaction. In order for such measurements to be carried out, the liquid is placed in a receptacle and exposed to a light beam. Light which is transmitted through the liquid is then analysed and characteristics of the liquid can be determined based on this analysis. The analytical procedure may involve single-point, multiple-point or time-resolved measurements.

Optical measurements are used in 'point of care' applications to analyse blood samples. A device is used to hold the sample relative to an optical unit (for producing a light beam and detecting transmitted or reflected light to infer, for example, the light absorbed or scattered by the liquid). Such devices may be microfluidic devices and/or may be centrifugal devices, such as 'lab on a disc' devices.

As well as obtaining an optical measurement of a liquid sample, such as a blood sample, it may be desirable to obtain a reference measurement also, for example a measurement of a buffer or saline solution, for comparison with the result obtained for the liquid sample. This can facilitate correction of results for imperfections in the receptacle in which the liquid is held, the material through which the light beam passes before and/or after passing through the liquid under measurement and/or imperfections in the optical unit, for example. It may also be advantageous to ascertain the optical properties of the reagents being used, in particular when these reagents are stored dry in the device and reconstituted at the moment of testing. Such reference measurements may enable the presence of substances in the sample which may interfere with the optical signal used for detection to be taken into account.

SUMMARY OF THE INVENTION

Aspects of the disclosure are set out in the independent claims. Further, optional features of embodiments are set out in the dependent claims.

In some aspects, there is provided a device for handling liquid. The device is configured for rotation about an axis of rotation to drive liquid flow within the device. The device comprises a detection chamber with a first end and a second end, the second end being opposed to the first end. The device further comprises two optical features, for example two reflective surfaces or diffractive surfaces with or without additional surfaces in between, defining an optical path through the detection chamber, from one of the first and second ends of the detection chamber to the other of the first and second ends of the detection chamber. The detection chamber comprises a first liquid inlet disposed at the first end of the detection chamber on a first side of the optical path, a first liquid outlet disposed at the second end of the detection chamber on the first side of the optical path and a second liquid outlet disposed at the second end of the detection chamber on a second side of the optical path. The first side of the optical path is radially outwards of the second side of the optical path.

Advantageously, this structure facilitates the replacement of one liquid in the detection chamber with another liquid, for example a reference liquid such as buffer solution, or different preparations of the sample or different samples. In particular, the positioning of one liquid outlet of the detection chamber on one side of the optical path and another liquid outlet of the detection chamber on the other side of the optical path facilitates the replacement of one liquid in the detection chamber with another and results in flow lines facilitating liquid exchange.

One advantage of replacing one liquid in a detection chamber with another liquid is that the same detection chamber can be used for measurement of both the sample and the reference liquid or for different samples/preparations. Advantageously, taking both measurements in the same chamber facilitates correction of the results for any imperfections in the detection chamber. Conversely, if one detection chamber was used for a reference measurement and a second, different chamber was used for measurement of the sample, any differences in the geometries of the two chambers, the dimensions relative to the optical path, or any imperfections in one chamber which are not present in the other could influence the results.

As mentioned above, one side of the optical path is radially outwards of the other side of the optical path, relative to the axis of rotation. The optical path may be disposed in a direction which has a tangential component as well as a radial component and may be non-parallel to the direction of action of the centrifugal force. In some embodiments, the optical path may be aligned tangentially or substantially tangentially and may be aligned in a direction perpendicular or substantially perpendicular to the direction of centrifugal force. An advantage of a configuration in which the optical path is aligned in a direction perpendicular or substantially perpendicular to the direction of centrifugal force is that the optical path (and hence the detection chamber) may have a smaller radial extent, i.e. a smaller extent along a radial direction in the device, for a given optical path length. This may be advantageous if other structures need to be implemented on the device. For example, the device may be disc-shaped or substantially disc-shaped and radial space on the disc may be limited.

In some embodiments, the device defines a plane containing the liquid handling structures of the device and the optical path is within the plane. For example, the device may be disc-shaped or substantially disc-shaped and the optical path may be within the plane of the disc. The optical path may be parallel or substantially parallel to the plane of the device.

It should be understood that the term 'optical path' refers to the path along which a light beam travels when the device is in use. It may also be defined as a notional normal joining the first and second reflective surfaces. At least part of this optical path may be used to probe liquid or otherwise gas contained in a detection chamber disposed between the optical features.

As mentioned above, the device is configured for rotation about an axis of rotation to drive liquid flow within the device. In some embodiments, the device comprises a feature which defines the axis of rotation and which is configured to be coupled to a rotational element to drive rotation of the device. For example, the device may be disc-shaped and may comprise a central hole defining the axis of rotation. The hole may be configured to engage with a drive mechanism for driving rotation of the device.

As described above, the first liquid outlet and the first liquid inlet of the detection chamber are disposed on a first side of the optical path and the second liquid outlet of the detection chamber is disposed on a second side of the optical path, the first side being radially outwards of the second side. The liquid inlet and one of the liquid outlets are on a side of the optical path which is radially outwards of the other side of the optical path, on which the other of the two liquid outlets is disposed. By positioning the liquid inlet on a radially-outer side of the optical path, the chances of removing the first liquid from the volume through which the light beam passes and filling that volume entirely (or at least substantially) with the second liquid is increased because the volume is filled radially inwards. This helps to maintain a clear boundary between the first and second liquids and reduces the mixing of the two liquids.

In some embodiments, one or both of the first liquid outlet and the first liquid inlet are disposed at a radially-outermost aspect of the detection chamber.

In some embodiments the second liquid inlet is disposed at a radially-innermost aspect of the detection chamber.

In some embodiments, the device comprises a cavity and the detection chamber is disposed within the cavity. For example, the cavity may contain one or more elements, such as pillars extending between a floor and a ceiling of the cavity, which define the detection chamber within the cavity between them. For example, the cavity may be defined between axially spaced surfaces, in which case the elements may be pillars extending in an axial direction between the axially spaced surfaces to define the detection chamber between facing surfaces of the pillars and the axially spaced surfaces.

In some embodiments, the device comprises a first element disposed in the cavity on a first side adjacent to the first end of the detection chamber and a second element disposed in the cavity on a second side adjacent to the second end of the detection chamber. Each of the two optical features is disposed in a respective one of the first and second elements. The detection chamber is thus disposed between the first element and the second element.

In some embodiments, the first and second optical features may each comprise an indent in the body of the device in the region of each element to form an angled wall for reflecting light from outside the device into a plane of the device and/or for reflecting light from within a plane of the device back out of the plane of the device. The reflective surface of the optical features may be reflective by virtue of the difference in refractive indices of air and of the material of the body or may be fully or partially silvered or have some other reflective coating.

In some embodiments, the cavity comprises a second liquid inlet on the first side of the cavity and the second element has a first side facing the first element and a second side opposed to the first side. A first wall of the cavity adjacent to the second side of the second element extends radially inwards of the second element. The second liquid inlet is disposed radially inwards of the first wall and the first element extends radially inwards of the second liquid inlet. Thus, the first liquid inlet is defined by a gap between the first element and a wall of the cavity. In some embodiments, the first liquid outlet is defined by a gap between the second element and a wall of the cavity and a radially-outer aspect of the second liquid outlet is defined by a radially-inner wall of the second element.

The second liquid inlet is disposed radially inwards of the first wall so that liquid is able to flow over (i.e. radially inwards of) the second element. The first element extends radially inwards of the second liquid inlet so that on entering the cavity via the second liquid inlet, liquid flows radially outwards, around the first element, rather than flowing radially inwards of the first element.

This structure provides a compact configuration for the detection chamber which is also easy to manufacture.

As mentioned above, a first wall of the cavity adjacent to the second side of the second element extends radially inwards of the second element. In some embodiments, a further wall of the cavity, extending from a radially inner end of the first wall, extends away from the second element, either radially outwards from the first point or in a circumferential direction from the first point.

In some embodiments, the first wall of the cavity extends radially inwards of the second element to a crest. A further wall of the cavity extends radially outwards from the crest. This feature may otherwise be referred to as an overflow. By positioning the overflow (crest) radially inwards of the second element (i.e. radially inwards of the second liquid outlet), the overflow is radially inwards of both the first and second liquid outlets and as a result, liquid flows out of the detection chamber via both of the first and second liquid outlets and then over the overflow (crest). The first liquid outlet (which is radially outwards of the second liquid outlet) is not favoured over the second liquid outlet due to its radial position relative to that of the second liquid outlet.

In some embodiments, the cavity comprises a second, radially-outer wall and a portion of the second wall between the first and second elements is radially inwards of a portion of the second wall facing the first element. In some embodiments, the portion of the second wall facing the first element may face a radially outer portion of the first element. The term 'between' as used with reference to this embodiment should be understood to mean circumferentially between, but not necessarily in between in a radial sense. The circumferential position of the portion of the second wall is between the respective circumferential positions of the first and second elements. The radial position of the portion of the second wall may or may not be fall within the radial extent of the first and second elements.

Advantageously, this configuration has the effect that liquid is guided into the detection chamber in a radially inwards direction. Accordingly, liquid already present in the detection chamber (which is radially inwards) is displaced, rather than liquid simply flowing along a radially-outermost aspect of the detection chamber.

In some embodiments, the device comprises an inlet conduit in communication with the second liquid inlet and the inlet conduit is sloped radially inwards.

In some embodiments, there is provided a method of taking an optical measurement of a liquid in a device as described herein. The method comprises rotating the device to cause at least a portion of a first liquid to flow into the detection chamber via the first liquid inlet and, as a result, at least a portion of a second liquid, which is present in the detection chamber, to flow out of the detection chamber via the first and second liquid outlets.

In some embodiments, there is provided a method of taking an optical measurement of a liquid in a device as described herein. The method comprises rotating the device to cause at least a portion of a first liquid to flow into the detection chamber via the first liquid inlet and, as a result, at least a portion of a second liquid, which is present in the detection chamber, to flow out of the detection chamber via the first and second liquid outlets.

In some embodiments, the method comprises, prior to rotating the device to cause at least a portion of a first liquid to flow into the detection chamber via the first liquid inlet and, as a result, at least a portion of a second liquid, which is present in the detection chamber, to flow out of the detection chamber via the first and second liquid outlets, obtaining a first optical measurement of the second liquid in the detection chamber. The method also comprises, subsequent to rotating the device to cause at least a portion of a first liquid to flow into the detection chamber via the first liquid inlet and, as a result, at least a portion of a second liquid to flow out of the detection chamber via the first and second liquid outlets, obtaining a second optical measurement, of the first liquid in the detection chamber.

In some embodiments there is provided a liquid handling system comprising a motor, a device as described herein, an optical unit for obtaining an optical measurement of a liquid in the device and a controller coupled to the motor to control rotation of the device. The controller is configured to implement methods as described herein.

The first and second liquids can each be any liquid. Examples include a blood sample (whole or lysed blood), blood plasma, urine, serum, dilutions of the same, particle suspensions (e.g. latex beads, nanoparticles), reaction mixtures, saline solution or another buffer.

In some embodiments, the device is a microfluidic device. For the avoidance of doubt, the term "microfluidic" is referred to herein to mean devices having a fluidic element such as a reservoir or a channel with at least one dimension below 1 mm. The device may be configured to handle volumes of liquid on the scale of nanoliters to microliters. Some but not necessarily all of the liquid handling structures on such a device may be microfluidic. For example, a length of the detection chamber may be approximately 1 cm. More specifically, a length of the optical path through the liquid in the detection chamber may be 1 cm. In some embodiments, a distance between the first reflective surface and the second reflective surface, through the detection chamber, is 1 cm. In some embodiments, the distance between the first reflective surface and the second reflective surface, through the detection chamber, is greater than or equal to 1 cm.

As used herein, the term 'outlet' should be understood to refer to any feature via which liquid leaves a chamber or area of the device 2. For example, an outlet could be an opening in a wall of a chamber or cavity, an opening or gap between two pillars, an opening or gap between an element or a pillar and a wall of a cavity or chamber or a connection between a conduit or channel and a chamber or cavity. The term "conduit" used herein can thus be understood accordingly as being configured to provide any suitable passage for liquid to an inlet or from an outlet, for example a channel, a space between features, such as walls, pillars, elements, etc., in accordance with various embodiments described herein.

As used herein, the term 'pillar' refers to a column which extends between the top and bottom of a chamber or cavity. For example, in embodiments in which the device is disc-shaped or substantially disc-shaped, the pillar may extend between the top and bottom of a chamber or cavity, perpendicular to the plane of the disc, in which liquid flows.

It will be understood that reference to a structure 'A' being disposed radially inwards of a structure 'B' should be taken to mean that a distance between structure 'A' and the axis of rotation of the device is less than a distance between structure 'B' and the axis of rotation of the device.

Equally, it will be understood that, reference to a structure 'A' being disposed radially outwards of a structure 'B' should be taken to mean that a distance between structure 'A' and the axis of rotation of the device is greater than a distance between structure 'B' and the axis of rotation of the device.

It will be understood that reference to a structure extending radially inwards should be taken to mean that the structure extends towards the axis of rotation. Equally, it will be understood that reference to a structure extending radially outwards should be taken to mean that the structure extends away from the axis of rotation

BRIEF DESCRIPTION OF THE FIGURES

The following description of specific embodiments is made by way of example and illustration and not limitation, with reference to the drawings in which:

With reference to FIG. 1A, a liquid handling device 2 comprises a detection chamber 6 with a first end and a second end. The second end of the detection chamber 6 is opposed to the first end. An inlet conduit 4, for example a channel or other passage, is connected to the detection chamber 6 via a first liquid inlet 8 of the detection chamber 6. The first liquid inlet 8 is disposed at a radially-outermost aspect of the detection chamber 6, at the first end of the detection chamber. The device further comprises a first optical feature comprising a reflective surface 10 at the first end of the detection chamber and a second optical feature comprising a reflective surface 12 at the second end of the detection chamber. The first reflective surface 10 is configured to direct a light beam which is incident upon the first reflective surface 10 from outside the device 2 towards the second reflective surface 12. The second reflective surface 12 is configured to direct a light beam which is incident upon the second reflective surface 12 from the first reflective surface 10 back out of the device 2. The first and second reflective surfaces define an optical path 14 through the detection chamber 6. The optical path 14 is, of course, part of a longer optical path from a light source to the optical feature, from one of the optical features to the other, possibly through the device before and after the optical feature, and back to a light detector. This has not been illustrated in the drawings for the sake of clarity.

Figure 1A:
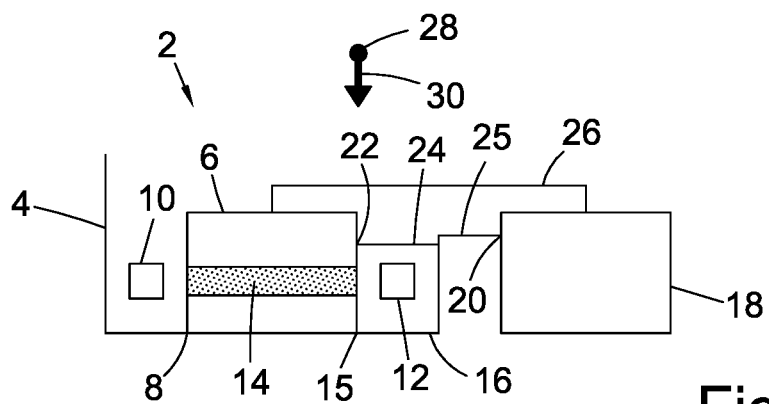
FIG. 1A illustrates schematically a device comprising a detection chamber.

In some embodiments in which the device comprises a body, for example a polycarbonate body, in which the various features are formed, for example in the shape of a disk, the full optical path starts substantially at an emitter, travels through air, enters the disk at an angle as close as possible to the normal to the disk plane so as to avoid deflection as light enters the disk, travels inside the polycarbonate until finding an inclined surface at 45 degrees at which, due to the refractive index difference between the plastic and air on the other side of the 45 degree surface, the light beam is total internally reflected in the disk plane. Light continues to travel in the plastic until the first wall of the detection chamber (which may be a wall substantially parallel to the axis of rotation or substantially normal to the disk to avoid deflection at the interface and may be optically flat), enters the detection chamber and travels through the liquid (or air if the chamber is empty) and exits the detection chamber through the opposite wall (which, again, may be vertical, i.e. substantially parallel to the axis of rotation, and optically flat), travels through the plastic until the second 45 degrees inclined surface deflects the light so that it travels though the thickness of disk and exits the disk, finally travelling through air to the detector.

The detection chamber 6 further comprises a first liquid outlet 15 which is connected to a first liquid outlet conduit 16 for example a channel or other passage. The first liquid outlet 15 is disposed at a radially-outermost aspect of the detection chamber 6, at the second end of the detection chamber.

The detection chamber 6 further comprises a second liquid outlet 22 disposed at the second end of the detection chamber. The second liquid outlet 22 is connected to a second liquid outlet conduit 24, for example a channel or other passage. The second liquid outlet conduit 24 is connected to the first liquid outlet conduit 16 and the two outlet conduits (16 and 24) combine to form a common conduit 25. The common conduit 25 is connected to a downstream liquid handling structure 18 via an inlet 20. The inlet 20 of the downstream liquid handling structure 18 is radially inwards of the second liquid outlet 22. In some embodiments, the second liquid outlet 22 may be disposed at a radially-innermost aspect of the detection chamber.

The device 2 further comprises an air conduit 26 for example a channel or other passage allowing the exchange of air, which connects the detection chamber and the downstream liquid handling structure 18. The air conduit 26 is connected to the detection chamber 6 at a radially-innermost aspect of the detection chamber and to the downstream liquid handling structure 18 at a radially-innermost aspect of the downstream liquid handling structure 18. The air conduit 26 is configured to allow air which is displaced by the flow of liquid from the detection chamber 6 to the downstream liquid handling structure 18 to escape back into the detection chamber 6 and may be in communication with the atmosphere outside the device or an internal air circuit of the device.

The device 2 is configured to be rotated about an axis of rotation 28 in order to impart a centrifugal force on liquid in the device 2 in order to cause it to flow through the device 2. The direction of the resulting centrifugal force is illustrated by arrow 30. In that sense, it will be understood that FIGS. 1A to 1C, and FIG. 3 below, can be seen as a schematic and/or developed view.

In some embodiments, the device 2 comprises a feature which defines the axis of rotation and this feature is configured to engage with a driving mechanism for driving rotation of the device. For example, the device 2 may be disc-shaped and may comprise a central hole defining the axis of rotation. The hole may be configured to engage with a drive mechanism for driving rotation of the device.

The structure may also be described in terms of the flow paths into and out of the detection chamber. A first flow path into the detection chamber 6 via the first liquid inlet 8 joins the detection chamber 6 at a first end of the detection chamber and at a radially-outermost aspect of the detection chamber. A first flow path out of the detection chamber 6, via the first liquid outlet 15, is connected to the detection chamber at a second end of the detection chamber and at a radially-outermost aspect of the detection chamber. A second flow path out of the detection chamber 6 via the second liquid outlet 22 is connected to the detection chamber at the second end of the detection chamber. The second flow path may be connected to the detection chamber at a radially-innermost aspect of the detection chamber.

Figure 2:
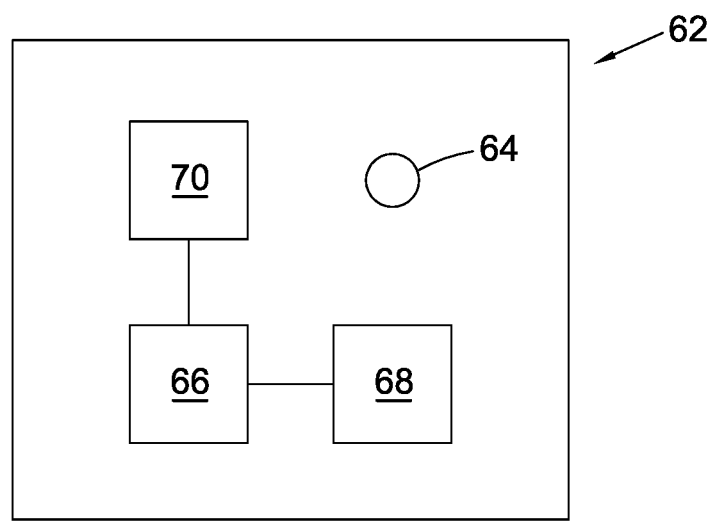
FIG. 2 illustrates schematically a drive system configured for use with a device as described herein.

With reference to FIG. 2, a system 62 for driving liquid flows in the device 2 and for taking optical measurements of liquid in the various detection chambers of the device 2 in accordance with the embodiments described above comprises a device engaging feature 64, for example a spindle with spring-loaded prongs for engaging a corresponding feature of the device, a tray and hub arrangement or any other arrangement for engaging the device 2, for example as commonly found in CD or DVD drives. The engaging feature 64 is coupled to an electric motor 70 which is controlled by a controller 66 configured to implement rotational speed protocols to drive liquid flows as described above.

The controller 66 is also coupled to and controls optical measurement unit 68 which is configured to generate a light beam and direct the light beam towards the device 2 and, in particular, to one of the optical features in the device 2. The optical measurement unit 68 is also configured to receive the light beam reflected back from the device and to measure the intensity of the light.

Figure 3:
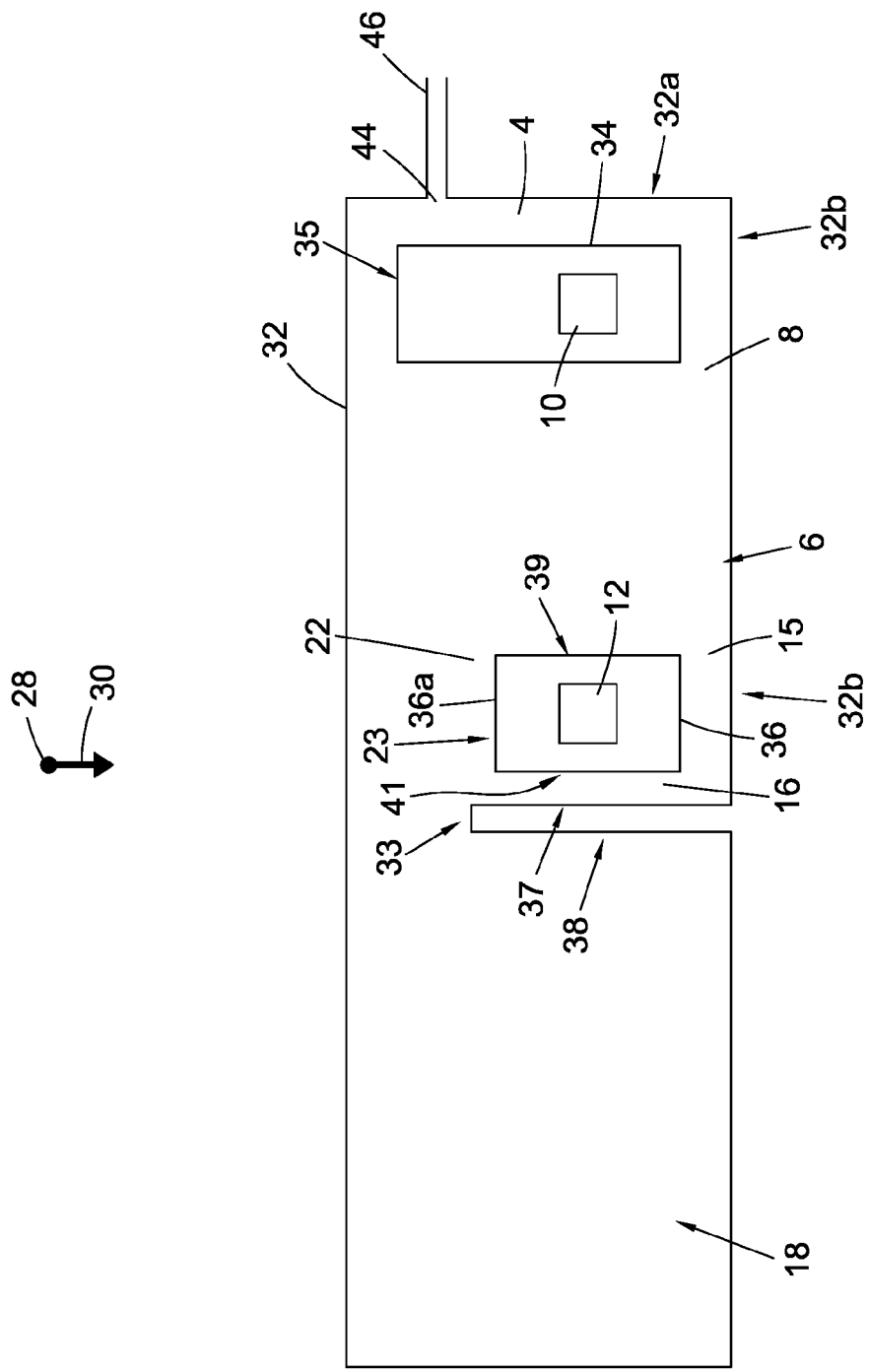
FIG. 3 illustrates schematically a further embodiment of a detection chamber.

Another embodiment of a detection chamber as described herein is shown schematically in FIG. 3. The embodiment is similar to that shown in FIG. 1A in a number of ways. In the embodiment illustrated in FIG. 3, the various inlets and outlets and inlet and outlet conduits of the embodiment shown in FIG. 1 are formed by a cavity containing two elements, as will now be described. The cavity may be defined between axially spaced surfaces of the device (i.e., spaced along the axis 28), which can be pictured parallel to the plane of the drawings in FIG. 3 and the elements may extend like pillars between the axially spaced surfaces. For the sake of ease of description, these elements will be referred to as pillars below. Accordingly, a number of the features of the structure shown in FIG. 1A are also present in that shown in FIG. 3. Like parts are labelled with like reference numerals and a description of these parts will not be repeated.

In the embodiment shown in FIG. 3, the detection chamber 6 is disposed within a cavity 32. The cavity 32 comprises an inlet 44, which is connected to an inlet conduit 46. A first pillar 34 is disposed within the cavity 32 on first side of the cavity 32 and a second pillar 36 is disposed within the cavity 32 on a second side of the cavity 32. The second pillar 36 has a first side 39, which faces the first pillar 34, and a second side 41 which is opposed to the first side of the second pillar. The first reflective surface 10 is disposed within the first pillar 34 and the second reflective surface 12 is disposed within the second pillar 36.

A wall of the first pillar 34 and a first side wall 32a of the cavity 32 define the inlet conduit 4, which is in communication with the first liquid inlet 8 of the detection chamber.

The first liquid inlet 8 is provided by a space or passage between the first pillar 34 and a second side wall 32*b* of the cavity 32.

A wall 41 of the second pillar 36 and a third side wall 37 of the cavity 32 define the first liquid outlet conduit 16, which is in communication with the first liquid outlet 15 of the detection chamber 6. The first liquid outlet 15 provided by a space or passage between the second pillar 36 and the second side wall 32*b* of the cavity 32.

The second liquid outlet 22 of the detection chamber 6 is adjacent to a radially inner wall 23 of the second pillar 36. In particular, a radially-inner aspect of the second liquid outlet 22 is provided by the radially inner wall 23 of the second pillar 36. In this way, the radially inner wall 23 of the second pillar 36 provides an overflow structure over which, in use, liquid flows.

The first pillar 34 extends radially inwards of the second pillar 36. In the embodiment shown in FIG. 3, a radially-inner wall 35 of the first pillar 34 is disposed radially inwards of a radially-inner wall 23 of the second pillar 36. The first pillar 34 also extends radially inwards of the liquid inlet 44 of the cavity 32.

The third side wall 37 of the cavity 32 adjacent to the second side 41 of the second pillar 36 extends radially inwards of the second pillar 36. The third side wall 37 extends radially inwards to a crest 33. A fifth side wall 38 of the cavity 32 extends from the crest 33 radially outwards. In this way, the wall of the cavity forms an overflow structure, over which any liquid radially inwards of the crest 33 flows over the crest. The crest 33 is disposed radially inwards of the second pillar 36.

The downstream liquid handling structure 18 is defined by further side walls of the cavity 32.

This structure may also be described in terms of the flow paths into and out of the detection chamber, as follows.

Two walls of the first pillar 34 and the first and second side walls 32*a,b* of the cavity 32 define a flow path into the detection chamber 6 via the liquid inlet 8. In particular, first and second side walls 32*a,b* and the walls of the first pillar 34 define a channel along which liquid flows into the detection chamber 6. The flow path into the detection chamber 6 extends around the first pillar 34, radially outwards of the first pillar. The respective walls of the cavity 32 and first pillar 34 may be parallel or substantially parallel. In some embodiments, a portion of the first flow path into the detection chamber upstream of the first liquid inlet is radially outwards of the first liquid inlet.

The third and second side walls 37, 32*b* of the cavity 32 and two walls of the second pillar 36 define a first flow path out of the detection chamber 6 via the first liquid outlet 15, around the second pillar, radially outwards of the second pillar 36. In particular, the third and second walls of the cavity 32 and two walls of the second pillar 36 define a passage along which liquid flows out of the detection chamber 6. The respective walls may be parallel or substantially parallel. In some embodiments, the first flow path extends radially outwards from the first liquid outlet 15.

A radially inner wall 36*a* of the second pillar 36 defines a second flow path out of the detection chamber 6 via the second liquid outlet 22. The second flow path extends around the second pillar 36, radially inwards of the second pillar. A radially-inner side of the second pillar 36 thus may form an overflow structure. In use, liquid flows over the second pillar 36, out of the detection chamber 6.

The first and second flow paths (via the first and second liquid outlets respectively) combine, traverse the crest 33 and pass into the downstream liquid handling structure 18.

Figure 4:
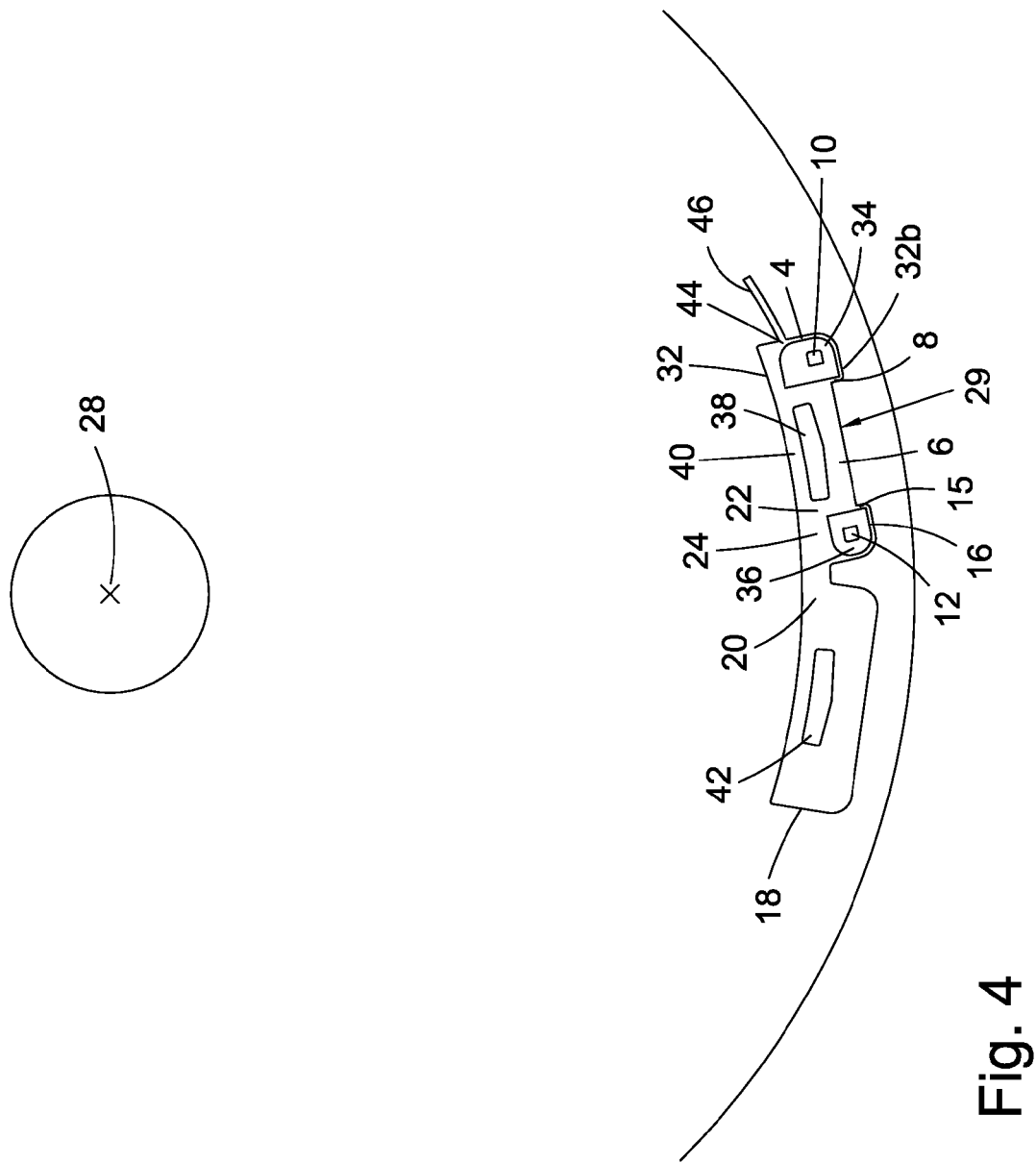
FIG. 4 illustrates an implementation of the structure illustrated schematically in FIG. 3.

An implementation of the structure shown schematically in FIG. 3 is illustrated in FIG. 4. Like parts are labelled with like reference numerals and these will not be described again here. Some additional features of the structure shown in FIG. 4 as compared to that shown in FIG. 3 and some features of the structure worth highlighting are as follows:

The device 2 comprises a third pillar 38 in the cavity 32 to provide structural support in the cavity 32.

The first liquid inlet 8 is disposed at a radially-outermost aspect of the detection chamber 6. The inlet conduit 4 extends radially inwards to the first liquid inlet 8. A portion 29 of the second wall 32*b* wall between the first and second pillars is radially inwards of a portion of the second wall 32*b* facing the first pillar. Advantageously, this configuration has the effect that liquid is guided into the detection chamber in a radially inwards direction. Accordingly, liquid already present in the detection chamber (which is radially inwards) is displaced, rather than liquid simply flowing along a radially-outermost aspect of the detection chamber.

The first liquid outlet 15 is disposed at a radially-outermost aspect of the detection chamber 6. The first liquid outlet conduit 16 extends radially-outward from the first liquid outlet 15. Advantageously, this facilitates the effective removal of a first liquid in the detection chamber from the detection chamber and its replacement with a second liquid. The first liquid outlet conduit 16 extends radially-outward from the first liquid outlet 15 and then radially inwards, around the second pillar 36.

A fourth pillar 42 is disposed within the downstream liquid handling structure 18 in order to provide structural support in the downstream liquid handling structure.

Figure 5:
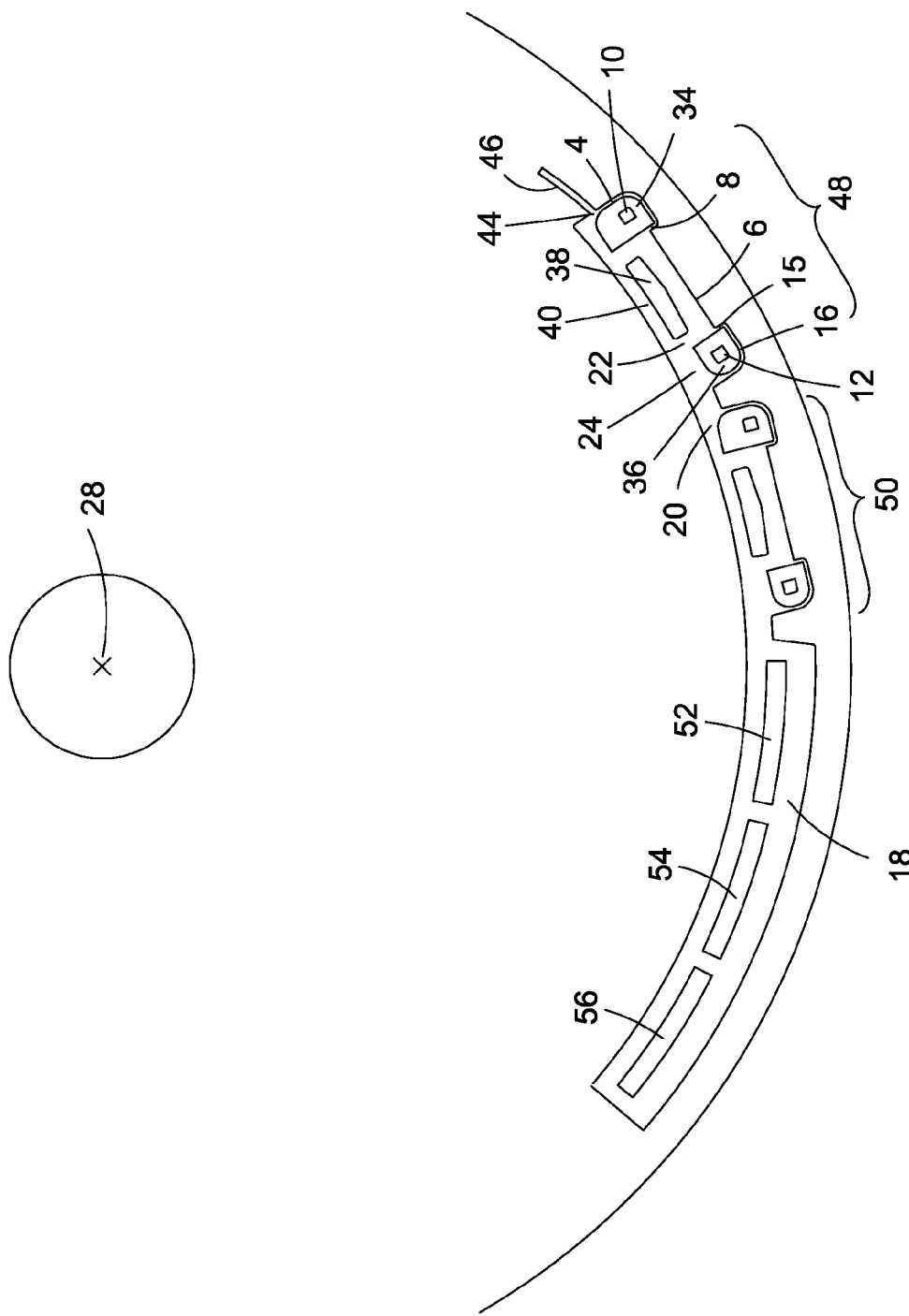
FIG. 5 illustrates another implementation with two detection chambers as described herein.

With reference to FIG. 5, another implementation of the structure shown schematically in FIG. 1A is described. In this embodiment, a first detection unit 48, which comprises the detection chamber 6, the first, second and third pillars 34, 36 and 38 the inlet conduit 4 and the outlet conduits 16 and 24, is connected to another such detection unit 50. This second detection unit 50 is in turn connected to a downstream liquid handling structure 18 (as described above), in which three pillars 52, 54 and 56 are disposed in order to provide structural support.

The detection chamber and related conduits have been described above, with reference to FIGS. 3, 4 and 5, as defined by certain side walls of the cavity 32 and walls of the pillars 35 and 36. It will, of course, be understood that the axially spaced walls of the cavity 32 also define the detection chamber there between.

Liquid flows in the device 2 and the corresponding method steps will now be described with reference to FIGS. 1B, 1C, 3 and 4.

Figure 1B:
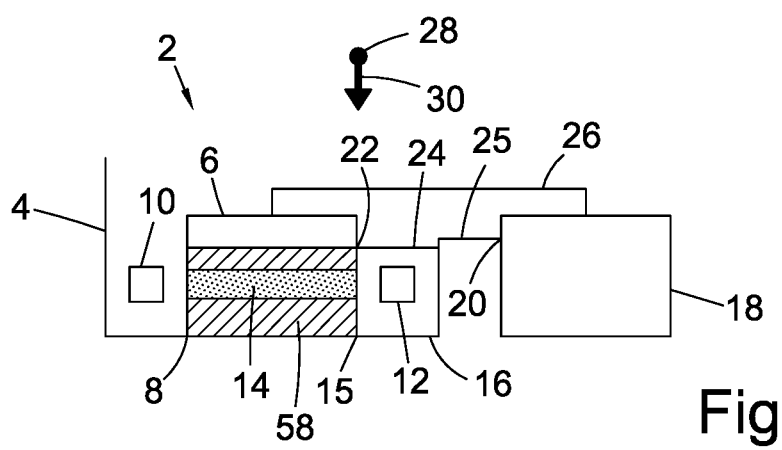
FIG. 1B illustrates schematically the device of FIG. 1A.

With reference to FIG. 1B, as a preliminary step, the device 2 is rotated in order to cause a first liquid 58 to enter the detection chamber 6 via the first liquid inlet 8. In some embodiments, the first liquid 58 may already be present in the detection chamber 6 and the preliminary step of causing the first liquid to enter the detection chamber 6 may be omitted.

An optical measurement of the first liquid 58 in the detection chamber 6 is then taken. An optical measuring unit may be used to produce a light beam and direct the light beam onto the first reflective surface 10. The light beam is then directed by the first reflective surface 10 through the detection chamber 6 (and hence through the liquid 58 in the detection chamber) towards the second reflective surface 12.

The second reflective surface 12 then directs the light beam back out of the device 2, where it is measured.

Figure 1C:
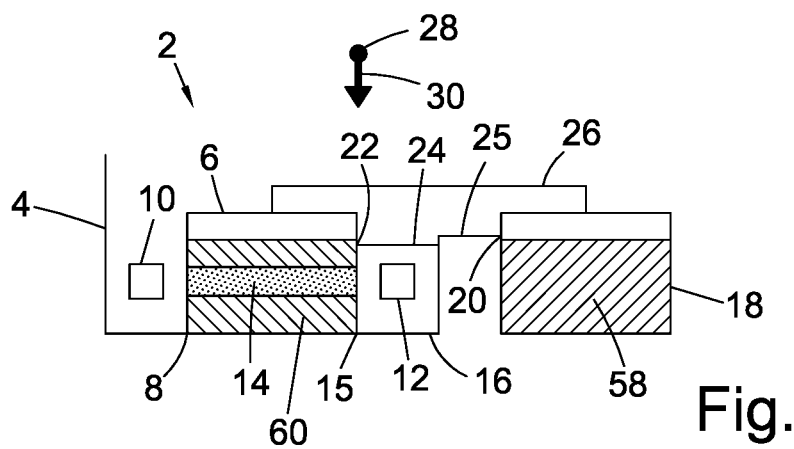
FIG. 1C illustrates schematically the device of FIG. 1A.

With reference to FIG. 1C, the device 2 is then rotated again (or rotation is continued) in order to cause a second liquid 60 to enter the detection chamber 6 via the first liquid inlet 8. In doing so, at least a portion of the first liquid 58 is forced out of the detection chamber 6 via the first and second liquid outlets 15 and 22 and into the downstream liquid handling structure 18. In some embodiments, all or substantially all of the first liquid 58 is forced out of the detection chamber 6 and into the downstream liquid handling structure 18. By positioning the outlets of the detection chamber one either side of the optical path 14, the chance that, after rotating to cause the second liquid to enter the detection chamber 6, the volume of the detection chamber through which the light beam passes will be entirely filled with the second liquid 60 is increased, the first liquid 58 having been forced out of the volume by the arrival of the second liquid 60.

An optical measurement of the second liquid 60 in the detection chamber 6 is then taken, in line with the method described above.

Liquid flows within the device shown in FIG. 4 are now described. The device 2 is rotated in order to cause a first liquid to enter the cavity 32 via inlet conduit 46 and inlet 44. Liquid flows into the first inlet conduit 4 and subsequently into the detection chamber 6 via the first liquid inlet 8. Under the action of centrifugal force, the detection chamber 6 fills with liquid. The device 2 is then stopped and a first optical measurement of the first liquid in the detection chamber 6 is taken.

The device 2 is then rotated again in order to cause a second liquid to enter the cavity 32 via the inlet conduit 46 and the inlet 44. The second liquid flows into the first inlet conduit 4 and as it does so, the second liquid displaces the first liquid and forces it along the conduit. The second liquid subsequently enters the detection chamber 6 via the first liquid inlet 8. The detection chamber 6 fills with the second liquid and as this happens, the first liquid in the detection chamber is displaced and forced out of the detection chamber 6 via the first and second liquid outlets 15 and 22. Liquid then overflows into the downstream liquid handling structure 18. A second optical measurement of the second liquid in the detection chamber 6 is then taken.

In the embodiment shown in FIG. 5, instead of liquid overflowing from the detection chamber 6 into the downstream liquid handling structure 18, liquid overflows into the second detection unit 50. The first liquid enters and fills the detection chamber of the second unit 50 in the same way as described for the first detection unit 48, with reference to FIG. 4. Meanwhile, the second liquid 60 fills the detection chamber 6 of the first unit 48 as described above. An optical measurement of the first liquid in the detection chamber of the second detection unit 50 and an optical measurement of the second liquid in the detection chamber 6 of the first unit 48 is then taken.

The device 2 can then be rotated again in order to cause a third liquid to enter the cavity 32 via the inlet conduit 46 and the inlet 44. This displaces the second liquid from the first unit 48 into the second unit 50, which in turn displaces the first liquid from the second unit 50 into the downstream liquid handling structures. In this way, a series of liquids can be caused to flow through the first and second units 48 and 50 and a number of optical measurements of the various liquids in the various detection chambers taken.

In some embodiments, the device 2 may comprise any number of detection units, such as units 48 and 50, connected in sequence.

The above description has been made in terms of specific embodiments for the purpose of illustration and not limitation. Many modifications and combinations of, and alternatives to, the features described above will be apparent to a person skilled in the art and are intended to fall within the scope of the invention, which is defined by the claims that follow.

For example, while conduits have been described above with reference to drawings depicting channel shaped conduits, it will be understood that the term "conduit" covers any arrangement providing a flow path conveying or conducting liquid from one part of the device to another. It will also be understood that the term "chamber" covers any arrangement which can contain liquid.

A cavity will be understood to be an empty space inside the device in which fluid can be contained or guided. An example of a cavity is a chamber.

The liquid handling structures in a device as described herein, such as the cavities, chamber and channels, are moulded or stamped in a substrate (which may otherwise be referred to as a carrier disc). A cover foil is then attached to the substrate to form the chambers and other structures. Equally, two discs may be joined together to form the liquid handling structures.

Specific embodiments have been described in which optical features used to direct light are provided in the form of reflective surfaces, for example based on total internal reflection or reflective coatings. Equally, the optical features may be provided by diffractive gratings to direct a diffraction order through the detection chamber. Likewise, while the optical path has been illustrated as a straight line between the optical features, the optical features may instead be configured such that light is directed through the detection chambers at an angle, for example to reflect one or more times from axially spaced walls of the detection chamber in between the optical features.

Where methods have been described above that require control of a drive system, the control steps may be implemented in software, hardware or a combination thereof, and may involve a single hardware component such as a general purpose processor or application specific integrated circuit or distributed in any way between a number of processors and integrated circuits. The components of the drive system may be provided in a single device or may be distributed in any suitable manner between a number of devices.

The invention claimed is:

1. A device for handling liquid, the device being configured for rotation about an axis of rotation to drive liquid flow within the device, the device comprising:
    a cavity;
    a liquid inlet into the cavity;
    a first element disposed in the cavity adjacent the liquid inlet and comprising a first optical element;
    a second element disposed in the cavity spaced from the first element and comprising a second optical element, wherein
    the first element, second element and a radially outer wall of the cavity define a detection chamber;
    the first and second optical elements define an optical path through the detection chamber there-between;
    a gap between the first element and the radially outer wall of the cavity defines a liquid inlet into the detection chamber;

a gap between the second element and the radially outer wall of the cavity defines a liquid outlet from the detection chamber;

a radially inner surface of the second element defines an overflow from the detection chamber;

a radially inwards extending wall of the cavity adjacent the second element extends radially inward of the second element to define a flow path from the liquid outlet around the second element;

the liquid inlet into the cavity is disposed radially inwards of the radially inwards extending wall; and the first element extends radially inwards of the liquid inlet into the cavity to define a liquid inlet conduit between the liquid inlet into the cavity and the liquid inlet into the detection chamber.

2. A device as claimed in claim 1, wherein a direction between the first and second elements is aligned substantially tangentially relative to the axis of rotation.

3. A device as claimed in claim 1, wherein the device comprises a feature which defines the axis of rotation and which is configured to be coupled to a rotational element to drive rotation of the device.

4. A device as claimed in claim 1, wherein a portion of the radially outer wall between the first and second elements is radially inwards of a portion of the radially outer wall facing the first element.

* * * * *